United States Patent [19]

Wardle

[11] Patent Number: 4,750,477
[45] Date of Patent: Jun. 14, 1988

[54] INSTRUMENT CONTROL HEAD

[75] Inventor: John L. Wardle, Shelton, Conn.

[73] Assignee: Circon Corporation, Santa Barbara, Calif.

[21] Appl. No.: 17,813

[22] Filed: Feb. 20, 1987

[51] Int. Cl.[4] .......................... A61B 1/00; A61B 1/06
[52] U.S. Cl. ............................................. 128/6; 128/4
[58] Field of Search ............................... 128/4, 5, 6, 7

[56] References Cited

U.S. PATENT DOCUMENTS

| | | | |
|---|---|---|---|
| 1,958,656 | 5/1934 | Buerger | 128/7 |
| 2,120,996 | 6/1938 | Wappler | 128/7 |
| 3,368,552 | 2/1968 | Bottcher | 128/4 |
| 3,792,701 | 2/1974 | Kloz et al. | 128/7 |
| 3,918,438 | 11/1975 | Hayamizu et al. | 128/4 |
| 4,188,942 | 2/1980 | Fehlberg | 128/6 |
| 4,207,873 | 6/1980 | Kruy | 128/6 |
| 4,439,030 | 3/1984 | Veda | 128/4 X |
| 4,704,007 | 11/1987 | Landre et al. | 128/6 X |

OTHER PUBLICATIONS

Operating and Maintenance Manual CDX-1 Rigi-Flex Choledochoscope.
Operating and Maintenance Manual G960 Rigi-Flex Nephroscope.
Operating and Maintenance Manual ACD-15, ACD-31 and G961 Rigi-Flex.

Primary Examiner—William H. Grieb
Attorney, Agent, or Firm—Perman & Green

[57] ABSTRACT

An instrument of a generally tubular flexible shape for accessing a target area comprising an objective head, a control head and a flexible shaft therebetween. The control head has a repositionable instrument entry block for inserting a surgical instrument or washing fluid into the control and to a target area near the objective head. The control head also has a repositionable light post and vent valve assembly which may be repositioned after the instrument has been inserted into a target area. The light post and vent valve assembly may also comprise a connector for a disconnectable external light carrier.

12 Claims, 6 Drawing Sheets

FIG. 3
FIG. 4
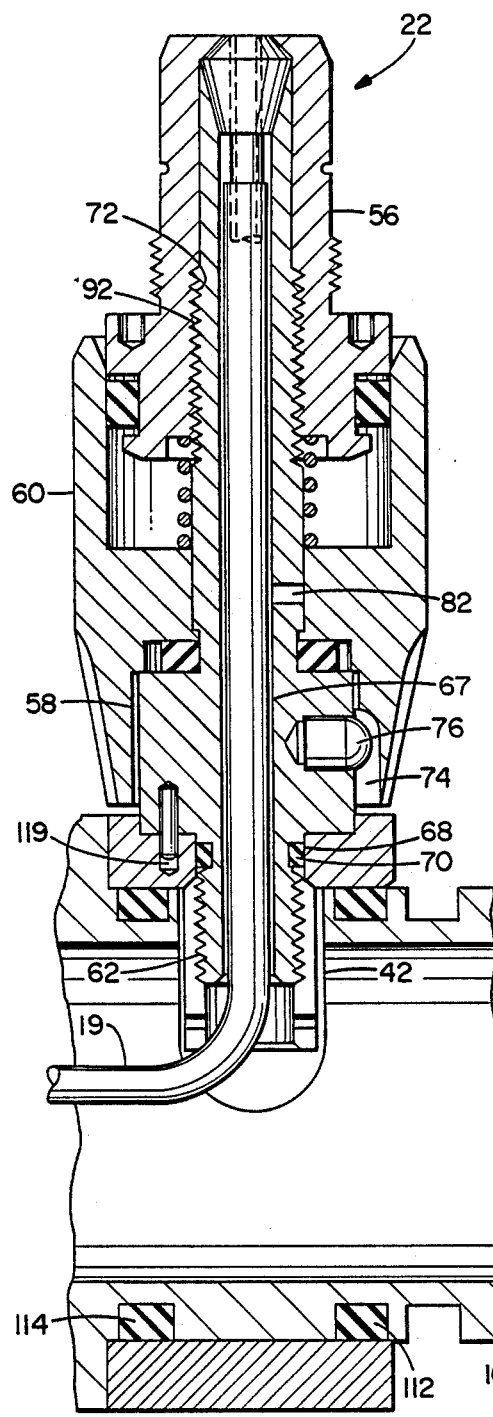
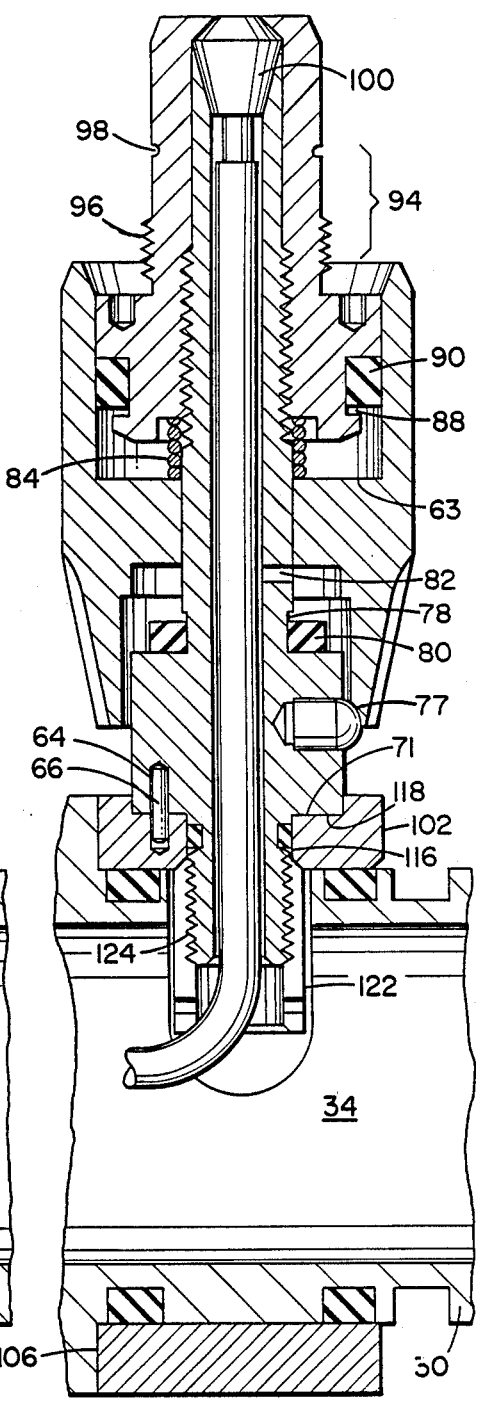

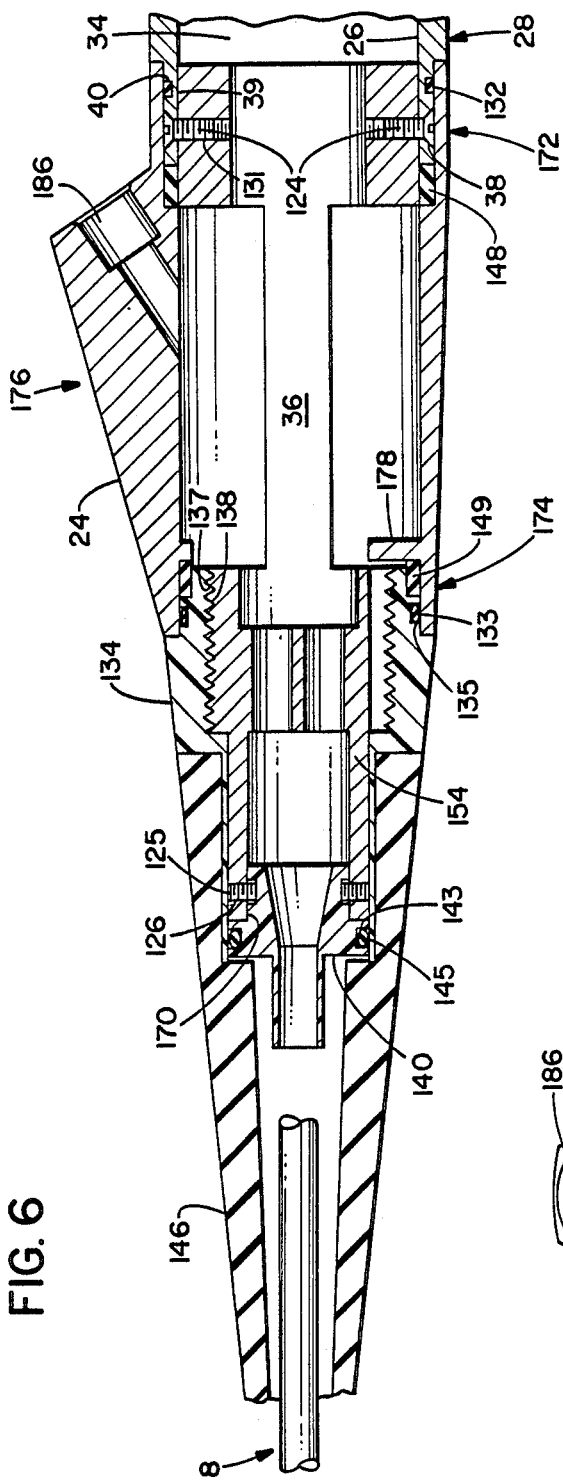

INSTRUMENT CONTROL HEAD

BACKGROUND OF THE INVENTION

1. Field of the Invention This invention relates to flexible inspection instruments for use in both industrial and medical applications and, more particularly, to an elongated, flexible, fiber-scopic inspection device having an improved control head with repositionable components.

Elongated tubular inspection devices, particularly such devices incorporating flexible fiber-optics, are often used to inspect sites which would not normally be visible to the human eye. One application of such tubular inspection devices is in the practice of medicine. For instance, a common form of such device, known as a flexible ureteroscope, is used for the inspection of the human ureter and kidney while a similarly structured device, known as a colonoscope, is used for the inspection of the colon.

The ureteroscope is conventionally used for a variety of functions such as observation of areas and presenting a working tool at the area for such things as removing ureteral or kidney stones, dislodgment or ultrasonic destruction of ureteral stones, taking biopsies, irradiating tumors with laser fibers, etc. The ureteroscope examination can involve the physician's placing the instrument in the body through the urethra, then into the bladder, then through one of the ureteral tubes and then, if necessary, into the kidney itself. This can usually be a long and potentially torturous path through several organs of the body.

The inspection instrument generally has a control head forming a proximal end and a flexible tubular shaft, the end of which forming a distal end. The physician observes target areas through an eyepiece in the control head. Generally, the ureteroscope is provided with a bundle or bundles of optical fibers which bring light to its objective end, the end which is placed adjacent the area to be examined, and a bundle or bundles of light transmitting fibers through which an image of the examined area is transmiited back to the eyepiece. The ureteroscope can generally further incorporate a channel which provides a conduit for providing washing fluid to the site under examination as well as for the introduction of accessory devices to the site such as a biopsy forceps.

The flexible tubular shaft extending between the proximal end and the distal end of the flexible instrument generally has a variety of components passing therethrough. The shaft may have such components as a fiber bundle, a working channel and distal end control wires. The tubular shafts can also have a variety of cross sectional shapes as is seen from U.S. Pat. Nos. 1,958,656; 2,120,996; 3,368,552; 3,792,701 and 3,918,438.

The control head of a flexible ureteroscope is generally capable of serving many purposes including housing the optical eyepiece assembly, providing an entry for a light carrier from a light source, housing a deflection control system for moving and controlling the distal end and providing an entry for tools and fluids to enter into the control head and be transported to the objective end by means of a working channel.

A problem arises in using presently available devices in that the control head of such devices are unalterable fixtures having rigid components such as a rigid entry block and rigid light carrier entry. The physician, however, must generally twist and turn the ureteroscope while it is being inserted into the patient to properly navigate a path to the target area. As a result, the light carrier entry to the instrument and wash/instrument entry at the control head can often be in an awkward position in which to effectively work. If the operator tries to reposition the control head he will probably lose his observation point in which to view the target area. If the instrument entry or the light carrier entry of the control head are in an awkward or hindering position the operator is nonetheless compelled to operate the instrument in this position because to attempt to move or twist the control head would result in a loss of sight of the target area and thus result in a loss of time in which to relocate the target area.

Hence, in the prior art, the operator generally was compelled to operate the instrument in the position in which the target area had been located. This problem is particularly acute in the flexible medical endoscopes such as ureteroscopes, cystoscopes, nephroscopes and choleodoscopes.

SUMMARY OF THE INVENTION

The foregoing problems are overcome and other advantages are provided by an instrument of a generally tubular shape for accessing a target area. The instrument has a control head with at least one portion thereof, such as an entry block or light carrier entry, which is repositionable relative to the control head.

In accordance with one embodiment of the invention, the tubular flexible instrument comprises a control head forming a proximal end, an objective head forming a distal end and a tubular flexible shaft therebetween.

The objective head is located at one end of the flexible shaft and is for observing and accessing a target area. The objective head has the end portions of at least two bundles of light transmittng fibers. The first bundle of fibers or series of bundles acts as a source of illumination providing light from an outside light source. The second bundle of fibers or series of bundles is for transmitting an image of the examined or target area back to an eye piece in the control head for viewing. Also contained in the objective head is an open area communicating with a working channel. The working channel travels from the control head to the objective head and allows a washing fluid or surgical instrument introduced at the control head to exit the objective head at the open area and thereby access the target area. The flexible tubular shaft extending between the control head and objective head is generally capable of conveying the objective head to the site to be examined. The shaft usually has a relatively short distal deflector section near the objective head and a relatively long proximal flexible section between the distal deflector section and the control head. The shaft provides a flexible housing for the working channel, the fiber optics bundles and the deflection control wires. The control wires are attached to a control section in the control head to adjust and deflect the distal deflector section in a controlled manner and thereby adjust and deflect the objective head.

The control head comprises a housing, an eyepiece assembly, a deflection control section, a rotatably mounted entry block and a light post and vent valve assembly. The light post/vent valve assembly provides an entry into the control head for a first bundle of light transmitting fibers. The fiber bundle transmits light from an exterior light source to the distal end and the area to be examined. The light post/vent valve assembly also provides a vent valve for immersion or gas sterilization of the instrument. The assembly may be rotatably mounted on the control head for repositioning the light post/vent valve assembly after the inspection instrument has been inserted into a patient for a less awkward and more easily obtainable position such that the physician will not be hindered by the assembly. The light post/vent valve assembly may also include a disconnectable external light carrier which can be connected and disconnected to the assembly and an integral light carrier.

The entry block provides an entry into the control head and entrance into a working channel for providing the target area with a wash or allowing an accessory instrument to access the target area. The entry block is rotatably mounted relative to the control head for repositioning the entry block after the inspection instrument has been inserted into the patient. The rotatable entry block thus provides for a less awkward and more easily obtainable position in which the physician or his assistant can operate the control head and use the entry block and its associated tools or accessories.

BRIEF DESCRIPTION OF THE DRAWINGS

The foregoing aspects and other features of the invention are explained in the following description, taken in connection with the accompanying drawings where:

FIG. 3 is a cross sectional side view of a light post/vent valve assembly attached to a control head with the valve in a closed position.

FIG. 4 is a cross sectional side view of the light post/vent valve assembly of FIG. 3 with the valve in an open position.

FIG. 6 is a partial cross-sectional side view of a forward portion of a control head, showing the rotatable entry block and its chassis assembly.

FIG. 9 is an end plain view of the entry block of FIG. 6.

DETAILED DESCRIPTION OF THE INVENTION

Figure 1:
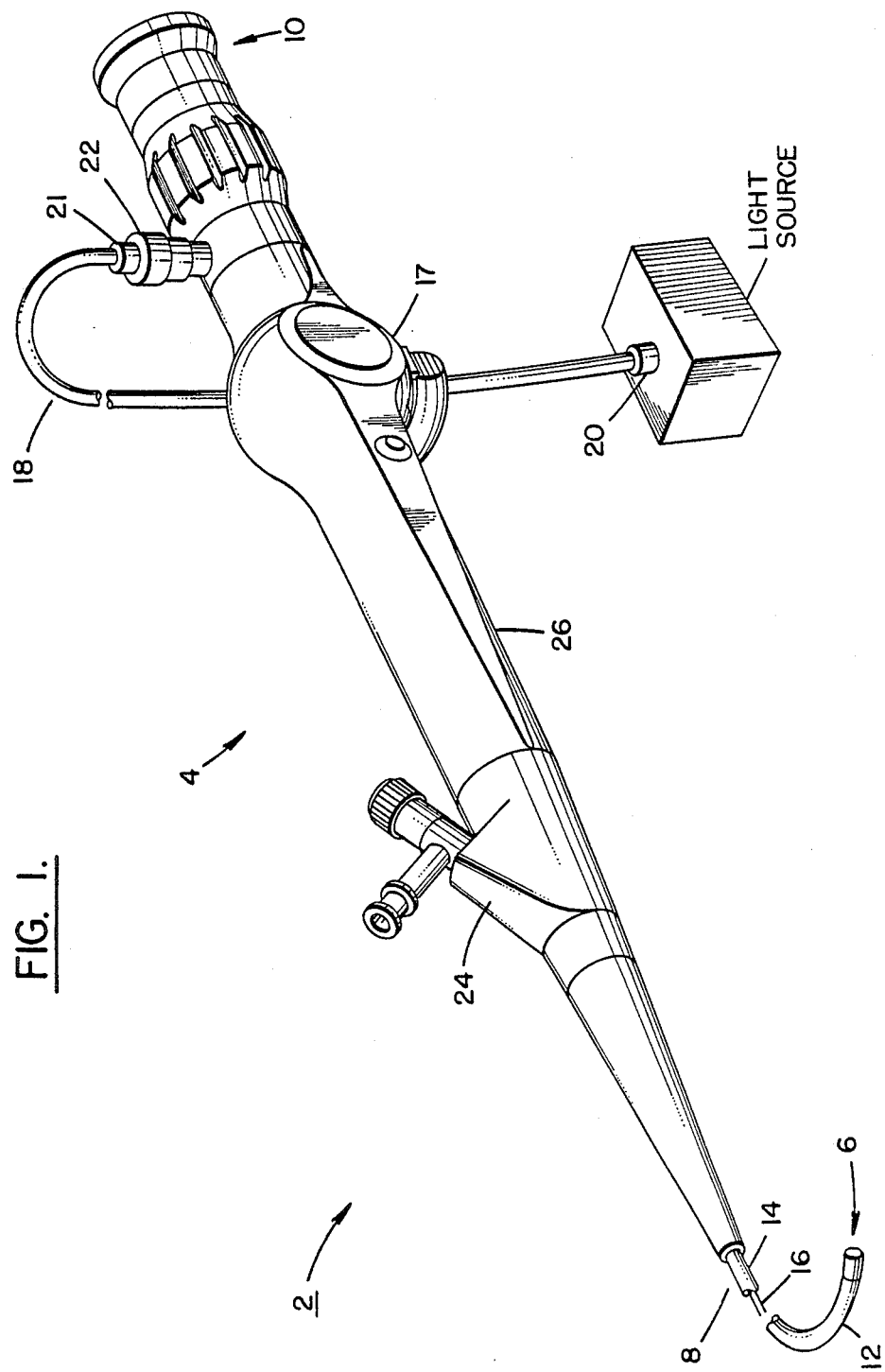
FIG. 1 is a perspective view of a flexible inspection instrument incorporating features of the present invention.

Referring to FIG. 1, there is shown one embodiment of a flexible inspection instrument 2, incorporating features of the invention. The inspection instrument 2, in this embodiment, is a flexible ureteroscope which is generally for internal examinations and operations on the human body and more particularly for use in the ureter and kidney area of the body. The ureteroscope 2 has a proximal control head 4 having a housing 26, a distal objective head 6 and a tubular flexible shaft 8 interconnecting the control head 4 to the objective head 6.

The tubular flexible shaft 8 is capable of conveying the objective head 6 to the site to be examined and is also capable of defining a tubular passage (not shown) for elongate components extending through the shaft from the control head 4 to the objective head 6. The tubular flexible shaft 8 includes a relatively short distal deflector section 12 connected to the objective head 6 and an extended proximal flexible section 14 between the distal deflector section 12 and the control head 4. The distal deflector section 12 is adjustable in a controlled manner from the control head 4 via a deflection control 17 and control wires 16 for manipulating the objective head 6 over the entire site, such as a body cavity, being examined and to this end has a high degree of flexibility. The flexible shaft section 14, however, is less flexible, being required to flex only sufficiently to follow the contours of the canal or tract leading to the target area.

For inspecting the site to be examined, in this embodiment, the ureteroscope has an optical system including an external light carrier or bundle of light transmittng fibers 18 for carrying light from a lamp box or light source for illuminating the inspection site. Light carrier 18 is connected to the lamp box by lamp box connector 20. In the embodiment shown, the carrier 18 has a control head connector 21 which attaches to a combination light post/vent valve assembly 22 on the control head 4. A second light carrier 19 (see FIG. 3) is located in the instrument 2 and receives light from the external light carrier 18 at the light post/vent valve assembly 22. The internal light carrier 19 travels through the control head 4 and through the flexible shaft 8 to the objective head 6. The carrier 19 then provides light to the inspection site. A light image received from the illuminated site is conveyed back to an eyepiece assembly 10 by a second internal light carrier and suitable optical system (not shown). Using the eyepiece assembly 10 the physician or clinician can view the operative field and follow the movement of the distal end of the flexible shaft relative to the operative field. In addition, the instrument 2 is further provided with an accessory passage or working channel 202 (see FIG. 8) which extends from the control head 4 through the flexible shaft 8 to terminate in an open end in the objective head 6 and is accessible through an entry block 24 mounted on the housing 26 of the control head 4.

Figure 2:
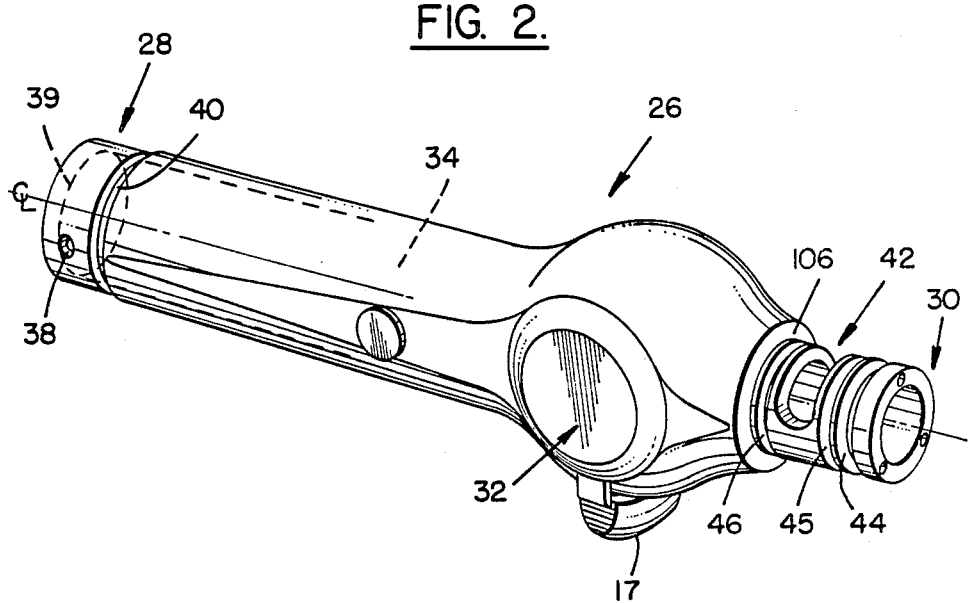
FIG. 2 is a perspective view of the control head housing of the instrument in FIG. 1.

Referring now also to FIG. 2, a perspective view of the housing 26 of the ureteroscope 2 in FIG. 1 is shown. The housing 26 in this embodiment is generally made of a metal, such as aluminum or stainless steel although any suitable material may be used. The housing 26 has a front end 28, a rear end 30 and a deflection control section 32. A passageway 34 travels from the front end 28 to the rear end 30. The deflection control 17 is housed in the deflection control section 32 of the housing. A typical flexible inspection instrument deflection control can be seen in U.S. Pat. No. 4,207,873 "Endoscope Deflection Control" by Kruy, which is incorporated by reference herein.

Figure 5:
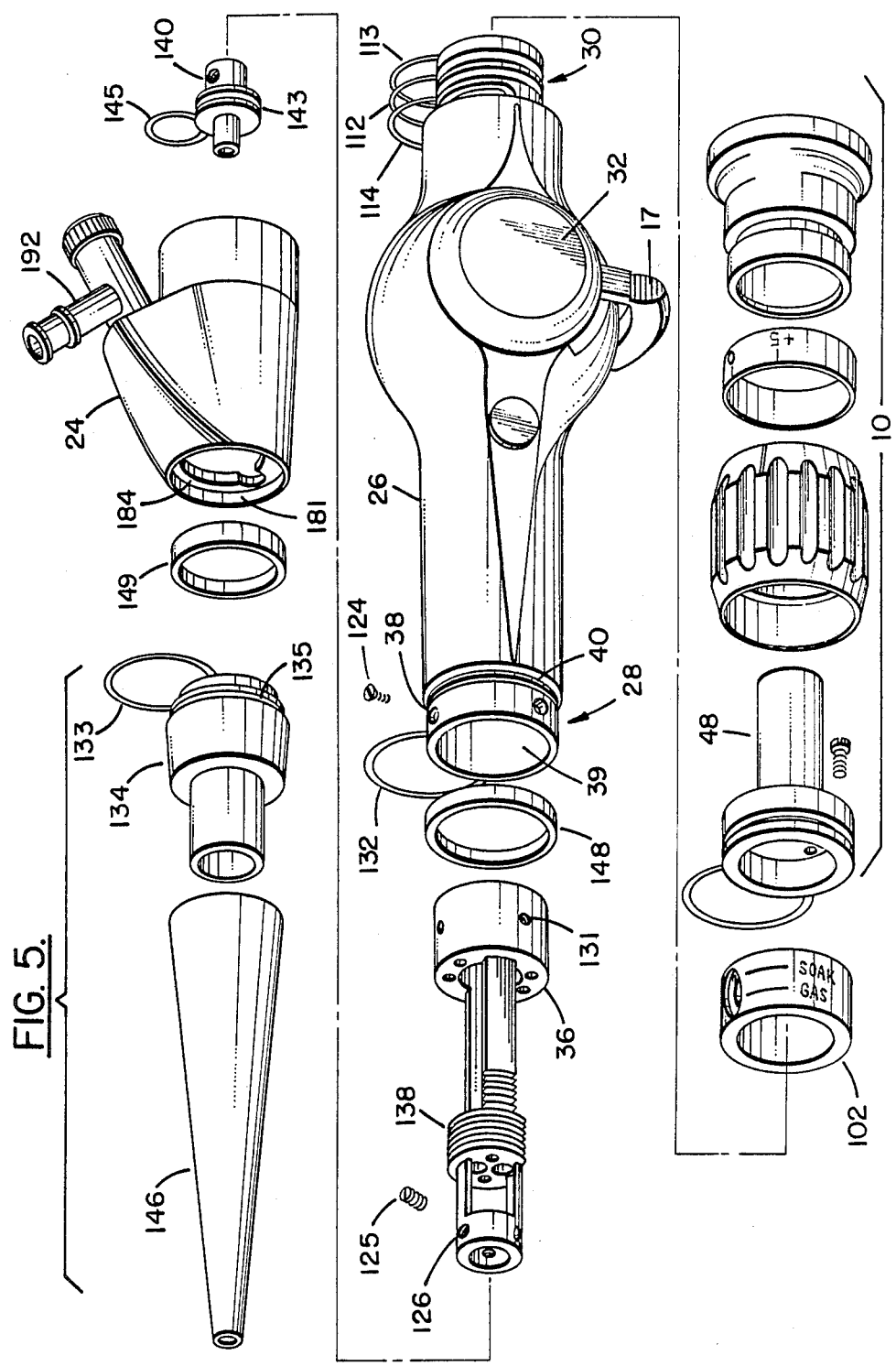
FIG. 5 is an exploded perspective view of the control head in FIG. 1.

The front end 28 of the housing 26 is generally circular in cross section and is for mounting the entry block 24 and an entry block chassis 36 (see FIGS. 5 and 6). The front end 28 has an entry block chassis aperture 39 for receivng at least a portion of the entry block chassis 36. The front end 28 also has mounting holes 38 for insertion of screws (not shown) into the entry block chassis 36 thereby fixedly attaching the entry block chassis to the housing 26. A seal receptacle 40 surrounds the housing 26 at the front end 28 for receiving and holding a seal (not shown) such as an O-ring. The seal provides a sealing engagement between the housing 26 and the entry block 24 in addition to providing at least a partial bearing and frictional surface for the entry block 24 to rotate about.

The frictional force generated by the seal between the housing 26 and entry block 24 is generally sufficient to prevent the entry block 24 from moving relative to the housing 26 without the operator purposefully repositioning the entry block. Thus the operator can reposition the entry block 24, but the entry block will otherwise remain stationary.

The rear end 30 of the housing 26 is for mounting the light post/vent valve assembly 22 and the eyepiece assembly 10. The rear end 30 is generally circular in cross section and has a portion of the housing passageway 34 passing therethrough. Adjacent the rear end 30 is a wall 106 formed by a difference between the outer cross sectional shapes of the rear end 30 and the deflection control section 32 of the housing 26. There are three seal receptacles 44, 45 and 46 located in the housing 26 at the rear end 30. The seal receptacles 44, 45 and 46 surround the outer circumference of the rear end 30 and are generally of a size and shape to receive a seal (see FIG. 4) such as an O-ring. The first seal receptacle 44 is for cooperating with a seal 113 and an eyepiece chassis 48 (see FIG. 5) for sealing the housing 26 to the eyepiece assembly 10.

Located between the second and third seal receptacles 45 and 46 at the rear end 30 of the housing 26 is a light post/vent valve assembly receiving slot 42. The slot 42 extends from the outside of the housing 26 into the housing passageway 34. The slot 42 is generally of a size and shape to receive at least a portion of the light post/vent valve assembly 22 and in the embodiment shown extends through the housing 26 approximately 180 degrees about the center axis.

Referring now to FIGS. 3 and 4, a cross-sectional side view of a light post/vent valve assembly 22 for mounting a disconnectable external light carrier, is shown. In this embodiment, the assembly 22 serves as an entry point for light from an external light carrier (not shown) to provide light to an internal light carrier 19 in the light post/vent valve assembly 22 and control head 4. The assembly 22 also serves as a vent when cleaning the inspection instrument 2 by gas sterilization. In addition, the vent can also be closed when the instrument 2 is cleaned in an immersion-type process.

The assembly 22 is generally made of metal parts, such as stainless steel, and has a light post 56, a vent valve body 58 and a vent valve knob 60. The vent valve body 58, in the embodiment shown, is generally circularly tower shaped and has an interior channel or passageway 67. The interior channel 67 provides a passageway for the internal light carrier 19 to travel through. In addition, the passageway also provides a path for venting the interior of the endoscope during a gas sterilization process. Air and other gases are allowed to exit and enter a vent 82 in the assembly 22. The valve body has two threaded portions 52 and 72. The first threaded portion 62 is provided for insertion into and retainment in the slot 42 in the housing rear end 30. Adjacent the threaded end portion 62 is a seal receptacle 68 for receiving and holding a seal 70 such as an O-ring seal. The vent valve body 58 has a bottom face 71 with a lock pin aperture 64. The lock pin aperture 64 is for receiving a lock pin 66 which prevents the light post/vent valve assembly 22 from rotational movement relative to a rotatable bushing 102. The bottom face 71 allows for tightly mounting the assembly 22 to the rotatable bushing 102 mounted to the housing. Before proceeding with a detailed description of the light post/vent valve assembly the rotational mounting of the assembly will be described.

In the embodiments shown in FIGS. 3 and 4, the rotatable swivel bushing 102 is mounted on the rear end 30 of the housing 26. The bushing 102 is generally ring shaped and has an internal cavity which is of a general size and shape to fit around the housing rear end 30. One side of the bushing 102 is adjacent the housing wall 106 at the rear end 30.

Also located in the rear end 30 are two seals 112 and 114 which are mounted in seal receptacles 45 and 46, respectively. The seals 112 and 114 form a sealing, bearing and frictional engagement between the housing 26 and the bushing 102. The bushing 102 also has a light post cavity 116 communicating through the bushing 102. The light post cavity 116 is of a general size and shape to allow the threaded end portion 62 of the light post/vent valve assembly 22 to pass through and into the slot 42 of the housing 26. The seal 70 located in the seal receptacle 68 on the assembly 22 sealingly engages the walls of the bushing 102 in the light post cavity 116. Located on the exterior of the bushing 102 is a seat 118 for receiving at least a portion of the face 71 of the vent valve body 58. Lock pin 66, mounted in the lock pin aperture 64 of the assembly 22 and a lock pin aperture 119 in the bushing 102, prevents the light post/vent valve assembly 22 from rotating relative to the bushing 102.

Located in the housing passageway 34 and slot 42 is retaining nut 122. The retaining nut 122 has a threaded portion 124 which mounts on the threaded end portion 62 of the vent valve body 58. The retaining nut 122, when attached to the assembly 22, also makes contact with the bottom of the bushing 102 and when the retaining nut 122 is tightened onto the light post/vent valve assembly 22 the nut 122 pulls the assembly 22 into the light post cavity 116 until the bottom face 71 of the assembly tightens onto the seat 118. The light post/vent valve assembly 22 thus mounted, is retained on the housing 26 and is rotatably mounted in such a manner that the assembly 22 and bushing 102 can rotate about the center axis of the control head 4. The rotation of the assembly 22 and bushing 102 can be limited by the engagement of the retaining nut 122 with either end of the slot 42 in the housing 26. In addition, the seals 112 and 114 provide sufficient frictional force on the bushing 102 to retain the assembly 22 and bushing 102 in a fixed position until the physician, by applying a directional force, decides to rotate the assembly 22.

Although the rotatable light post/vent valve assembly 22 has been described in detail, the features of the rotatable assembly 22 may be embodied in many different ways. The assembly 22 could be mounted at another suitable location on the control head 4, in either a fixed position or a rotatable position as described herein. Any suitable type of repositioning means could be used on the control head 4. And the repositioning means might allow for about a 360 degree allowable arc or rotation.

Referring back to the light post/vent valve assembly 22. The light post 56 is mounted on the valve body 58 by means of the second threaded portion 72 on the valve body 58 and a threaded section 92 in the light post 56 which cooperate to mount the post 56 to the body 58. The light post 56 also has a universal light souce connector section 94. The connector section 94 has mounting threads 96 and a clip depression 98 for mounting either a screw-on type connector (not shown), or a spring type connector (not shown), respectively. A seal receptical 88 and a seal 90 surround the post 56 and sealingly engage an internal portion of the knob 60. Seal 90 always retains a sealing engagement between the post 56 and knob 60 even when the knob 60 is adjusted. Mounted in the top of the assembly 22 is an end plug 100. The end plug 100 may generally be made of a resilient polymer material such as polytetrafluroethylene or Teflon; however, any suitable material may be used. The end plug 100 allows the fiber bundle or light carrier 19 to be retained in the assembly 22 while also sealingly engaging the carrier 19, the light post 56 and the valve body 58.

Mounted partially between and also partially surrounding the light post 56 and valve body 58 is the vent valve knob 60. The knob 60 is generally column shaped and has a varying open interior 61 for insertion of the light post 56 and the valve body 58. The knob 60 has an internal spring ledge 63 which supports a spring 84. The spring 84 is mounted around the valve body 58. One end of the spring 94 is in contact with the internal spring ledge 63 of the knob 60. The opposite end of the spring 84 is in contact with the light post 56 with the spring 84 at least partially compressed therebetween. The compression of the spring 84 forces the knob 60 to sealingly engage with a seal 80, such as an O-ring, in a seal receptacle 78 of the valve body 58. The seal receptacle 78 located in the vent valve body 58 holds the seal 80 and sealingly engages between the knob 60 and the valve body 58 when the vent valve is in a closed position as shown in FIG. 3. If the vent valve is in an open position as shown in FIG. 4, the sealing engagement between the seal 80, body 58 and knob 60 is broken to allow the vent 82 to communicate from the interior of the assembly 22 to the environment outside the assembly 22.

The seal 90, cooperating with the knob 60 and post 56, and the seal 80, cooperating with the knob 60 and body 58, are generally located at opposite positions from the vent 82. In a closed position, as shown in FIG. 3, the two seals 80 and 90 cooperate with each other and the post 56, knob 60 and body 58 to effectively prevent the vent 82 from accessing the outside of the assembly 22. In an open position, a position in which the vent 82 has access to the environment outside the assembly 22, the sealing engagement by seal 80 is broken. To open and close the vent, the knob 60 is pushed towards and away from the post 56. If the knob 60 is pushed towards the post 56 thereby compressing the spring 84 although the sealing engagement of the seal 90 is maintained, the sealing engagement between the valve post 58 and valve knob 60 with seal 80 is broken. The vent 82 can now communicate to the outside environment of the light post/vent valve assembly 22 and thereby prevent pressure differences between the interior of the endoscope and the outside environment from causing damage during the vacuum cycle of the gas sterilization. To retain the vent in an open position, the knob 60 has an open pin aperture 74 for receiving a portion of an open pin 76. The pin 76 cooperates with the valve knob 60 to allow the vent valve to remain open or closed. When the open pin 76 is in the open pin aperture 74 of the knob, the seals 80 and 90 effectively seal the vent 82 from the outside environment. After pushing the knob 60 towards the post 56 the knob 60 can also be rotated about the post 58 until open pin 76 rests on ledge 77 on the knob 60 wherein the open pin 76 can retain the knob 60 on ledge 77 and thereby maintain the open vent position. The knob 60 can then be rotated back to a position where the open pin 76 once again sits in the open pin aperture 74 and spring 84 can once again compress the knob 60 onto seal 80 thereby sealing the vent 82. The combination light post and vent valve assembly 22, thus allows the instrument 2 to be cleaned in either a gas sterilization process or a liquid immersion process. In a preferred embodiment, as shown in FIG. 5, appropriate markings are arranged on the bushing 102 and cooperating markings on the light post/vent valve assembly 22 (not shown) allow the operator to read and interpret the markings relative to each other to indicate whether the vent 82 in the light post/vent valve assembly 22 is open or closed or alternately whether the assembly 22 is set for gas sterilization or liquid cleaning.

The combination light post and vent valve assembly 22, as described above, provides an additional advantage by reducing the number of seals needed on the housing if the light post and vent valve were separate elements and therefore were separately mounted on the housing. In addition, the combining of the light post and vent valve allows the overall length of the control head 4 to be reduced and thereby provide easier handling, cleaning and transporting of the inspection instrument 2. Referring now to FIGS. 1 and 5 wherein FIG. 5 shows an exploded perspective view of the control head 4 of FIG. 1 without the light post/vent valve assembly 22 attached. The eyepiece assembly 10 and suitable optical means (not shown) is attached by means of an eyepiece chassis 48 to the housing 26. The bushing 102 is mounted over the rear end 30 of the housing with the seals 112 and 114 therebetween. At a forward section of the control head 4 the rotatable instrument entry block 24 is mounted on the control head 4.

Referring also to FIG. 6, a cross sectional side view of the forward section of the control head of FIG. 5 is shown. An entry block chassis 36 is partially mounted in the entry block chassis aperture 39 at the housing front end 28. Mounting screws 124 screw into holes 131 in the chassis 36 through the holes 38 to fixedly mount the chassis 36 to the housing 26. A seal 132, such as an O-ring, is retained in seal depression 40 at the housing front end 28. A spacer 148 is around the chassis 36 and adjacent the front end 28 of the housing 26. Mounted partially in the opposite end of the chassis 36 is a shaft end bushing 140. A screw 125 screws through holes 126 in the chassis 36 and into the bushing 140 to retain the bushing 140 in the chassis 36. A seal 145 is retained in a seal depression 143 in the bushing 140 for sealing engagement with a strain relief bushing 134. The strain relief bushing 134 is mounted on the chassis 36 by means of a threaded section 138 of the chassis 36 and a cooperating threaded section 137 of the strain relief bushing 134. Mounted on the strain relief bushing 134 is a strain relief 146 which has a portion of the flexible shaft 8 passing therethrough. Also mounted on the strain relief bushing 134 is a seal 133, such as an O-ring, contained in a seal depression 135 and a spacer 149. Rotatable mounted about the chassis 36 and between the housing 26 and strain relief bushing 134 is the entry block 24.

Figure 7A:
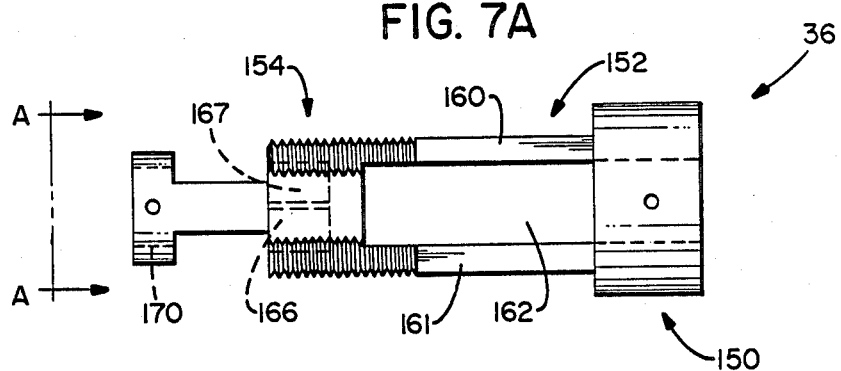
FIG. 7A is a bottom view of the entry block chassis shown in FIG. 5.

Referring to FIGS. 7a, b, c and d, the entry block chassis 36 of FIG. 5 is shown and will be described in more detail. The chassis 36 can be generally made of metal, such as aluminum or any other suitable material. FIGS. 7a and b show a bottom view and a side view of the chassis 36, respectively. In the embodiment shown, the chassis 36 has a housing connection section 150, a center span section 152 and a forward connection section 154. The housing connection section 150 has three mounting holes 131 for receiving screws (not shown) from the mounting holes 38 in the housing 26 thereby mounting the housing connection section 150 of the chassis 36 in the chassis aperture 39 adjacent the housing passageway 34. The housing connection section 150 also has a center passageway 158 that communicates from the housing 26 and housing passageway 34 through to the center span section 152 of the chassis 36.

Figure 7B:
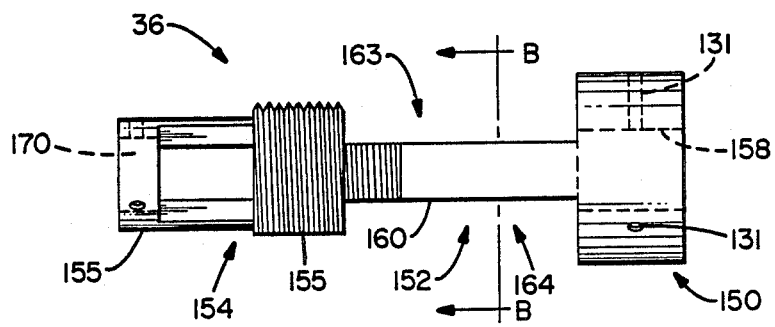
FIG. 7B is a side view of the entry block chassis in FIG. 7A.
Figure 7C:
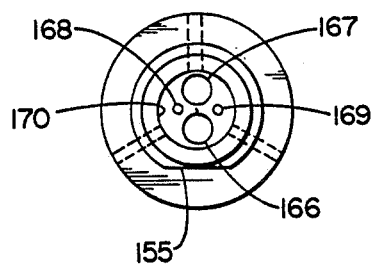
FIG. 7C is an end view of the entry block chassis in FIG. 7A taken along line A—A.
Figure 7D:
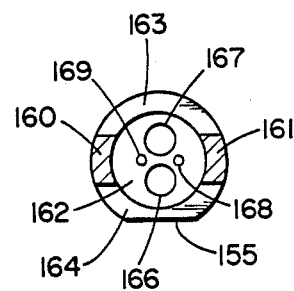
FIG. 7D is a cross-sectional view entry block chassis of FIG. 7B taken along line B—B.

Referring also to FIG. 7d, a cross-sectional view along line B—B of FIG. 7b is shown. The center span section 152 is connected at one end to the housing connection section 150 and at the opposite end to the forward connection section 154. The center span section 152 in this embodiment has two members 160 and 161. The two center span members 160 and 161 define a center span passageway 162 similar to the center passageway 158 in the housing connection section 150. However, the center span section 152 has an unobscured or open top 163 and bottom 164.

FIG. 7c also shows an end view of the chassis 36 along line A—A of FIG. 7a. The forward connection section 154 is attached to the center span section 152 and in this embodiment, has four passageways that pass through it; a fiber optics passageway 166, a working channel passageway 167, and two control wire passageways 168 and 169. The forward connection section 154 has a bottom 155 that is flat. The flat bottom 155 is provided to allow the entry block 24 to pass over the forward connection section 154 of the entry block chassis 36 during assembly of the control head 4 without any interference between the chassis 36 and a limiting member 178 on the entry block 24 (see FIG. 6). A shaft end bushing aperture 170 is provided at the forward connection section 154 for mounting the shaft end bushing 140.

Referring now to FIGS. 5, 6, 8 and 9, the entry block 24 will now be described. In the embodiment shown, the entry block 24 is rotatably mounted on the control head 4 between the housing 26 and the strain relief bushing 134. The entry block 24, in the embodiment shown may be generally made of metal, such as aluminum or stainless steel, but can be made of any suitable material. As best shown in FIG. 6, the entry block 24 has a housing rotational bearing section 172, a forward rotational bearing section 174, an instrument entry section 176 and a limiting stop member 178.

The housing rotational bearing section 172 is generally circular and is of a general size and shape to be mounted over the front end 28 of the housing 26 with the seal 132 therebetween. The block 24 has a center passageway 180 which allows the block 24 to be installed over the entry block chassis 36. A generally ring shaped space 148 is mounted on the chassis 36 between the chassis 36 and entry block 24. The spacer is provided as a bearing surface to allow the entry block to rotate without hindrance from the housing connection section 150 of the chassis 36 or the housing 26. A stop face 182 in the passageway 180 of the entry block 24 cooperates with the spacer 148 to properly position the entry block in relation to the housing 26 and chassis 36 to prevent damage to the parts during rotation.

The forward rotational bearing section 174 is also generally circular and of a general size and shape to accept a portion of the strain relief bushing 134 which is mounted on the entry block chassis 36 and is contained in at least a portion of a forward entry block passageway 181 of the entry block passageway 180. The generally ring shaped spacer 149 is mounted on the strain relief bushing 134 between the bushing 134 and the entry block 24. The spacer, similar to spacer 148, in cooperation with a stop face 184 in the entry block 24 allows the entry block 24 to be properly positioned in relation to the strain relief bushing and chassis 36 to allow rotation without interference from the strain relief bushing 134 or damage to any of the parts. Also contained between the bushing 134 and the entry block 24 is the seal 133 contrained in the seal receptacle 135 in the bushing 134. Seals 132 and 133 cooperate to allow the entry block 24 to be sealingly mounted to the control head 4 while also allowing the entry block 24 to be rotatably mounted. In addition, the seals 132 and 133 provide sufficient frictional force on the entry block 24 to retain the entry block in a fixed position until the physician, by applying a directional force, decides to rotate the entry block 24.

Located in the entry block passage 180 is a limiting stop member 178. The limiting stop member 178 is positioned in the bottom area 164 of the center span section 152 of the chassis 36. The stop member 178 cooperates with the two span members 160 and 161 of the chassis 36 to limit the amount of rotation of the entry block about the center axis of the control head. The chassis 36 being fixedly attached to the housing 26, the entry block 24 can rotate about the center axis of the control head until it makes contact with either span member 160 or 161. The entry block 24 is then prevented from rotating in the direction in which it made contact with the span member 160 or 161, but may rotate back in the opposite direction. The entry block 24 and entry block chassis 36 thus cooperate to allow the entry block 24 to rotate about the chassis 36 in a specified field or arc of rotation. In a preferred embodiment, the field of rotation of the entry block is limited to about a ninety degree arc.

Although the rotatable entry block 24 and control head 4 have been described in detail in this embodiment, the features of the rotatable entry block 24 may be embodied in many different forms. The entry block 24 might allow for about a 360 degree allowable arc or rotation. The entry block 24 might be mounted in a different location on the control head. Also, any suitable mounting means could be used including a mounting means which did not include an entry block chassis 36.

Figure 8:
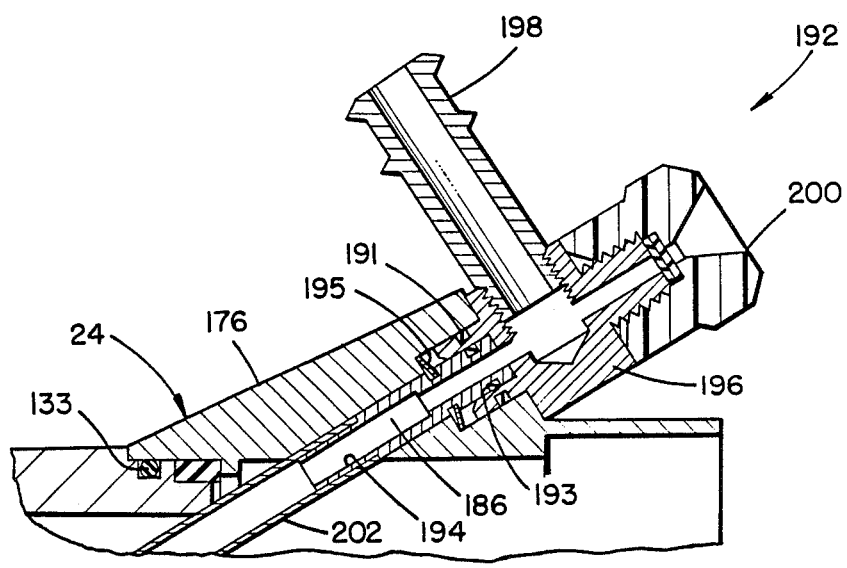
FIG. 8 is a partial cross-sectional view of the entry block in FIG. 6 having an instrument accessory attachment therein.

The instrument entry section 176 of the entry block 24 is provided for inserting a surgical instrument or washing fluid into the control head 4 and to the target area. The entry section 176 has an entry passage or aperture 186 for insertion of the instrument or fluid. Referring now also to FIG. 8, a partial view of the entry block 24 having an instrument accessory attachment 192 is shown. The instrument accessory attachment 192, in the embodiment shown, is for insertion of a forceps instrument and for introducing a wash fluid to the target area.

The instrument accessory attachment 192, in this embodiment, comprises a working channel end fitting 194, an irrigation post 196, an irrigation nipple 198 and an instrument seal housing 200. The working channel end fitting 194 is attached at one end to a working channel 202. The working channel 202, as described above, provides a channel for an instrument or fluid to travel from the control head to the target area. The fitting 194 is inserted into the aperture 186 and retained by a retaining ring 195. After the fitting 194 and retaining ring 195 have been inserted into the entry block 24 the irrigation post 196 is attached to the entry block 24 by screws (not shown). The end fitting 194 is then mounted partially in the irrigation post 196 with a seal 193, such as an O-ring, forming a seal between the two pieces. A seal 191, such as an O-ring, is located between the post 196 and the entry block 24 in the aperture 196 to form a sealing engagement between these two parts. The screws (not shown) that attach the post 196 to the entry block 24 and the retaining ring 195 cooperate to maintain the end fitting 194 in the entry block 24. The working channel 202 travels through the entry passageway 186, the chassis working channel passageway 167, the shaft end bushing 140 and the flexible shaft 8 to an opening in the distal end of the flexible shaft 8. An irrigation nipple 198 is mounted in the irrigation post 196 and can be attached to a means for supplying a washing fluid (not shown) or to other means such as a stopcock and fluid supply. Mounted on the end of the irrigation post 196 is the instrument seal housing 200 which allows a forcep to enter the control head 4 and also sealingly engages the forceps after it has entered.

In operation, the ureteroscope 2 can be inserted into a patient. The physician can observe the operative field at the objective head 6 by means of the optical system and eyepiece 10 of the ureteroscope 2. While the physician is inserting the ureteroscope 2 he may find it necessary to twist or turn the instrument 2 to properly navigate a path to the target area. After the distal end of the instrument 2 has reached the target area, the physician, rather than using the instrument with the light post and entry block in an awkward position, can rotate and reposition the entry block 24 to a position in which a surgical instrument or wash fluid can be easily inserted into the control head 4. In addition, the physician can also reposition the light post/vent valve assembly 22 to a position where it will not hinder or obstruct the physician's use of the instrument.

During cleaning of the ureterscope 2, the vent valve on the light post/vent valve assembly 22 can be maintained in either an open or closed position depending on whether the ureteroscope 2 is being cleaned by a gas sterilization method or an immersion method. Also, the external light carrier 18 may be disconnected from the ureteroscope 2 during cleaning, storage or transportation.

The above-described inspection instrument 2 is only one embodiment of the invention. As the embodiment illustrates, all of the features of the invention may be embodied in one instrument in addition to separate features of the invention being embodied in separate instruments or in any combination thereof. Any suitable material may be used in the different embodied parts of the invention and any suitable mounting means may be used to repositionally mount specific features of the invention.

It should be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. An instrument of a generally tubular flexible shape for accessing a target area, said instrument having a proximal end thereof, distal end thereof, and a working channel therebetween, said proximal end having a control head including an entry block means containing a portion of said working channel, said control head further comprising:

control head housing means having a passageway to permit access of said working channel from said entry block means through said control head housing means, and means for repositionally mounting said entry block means relative to said control head housing means while enabling said housing passageway to have access to said working channel, whereby said entry block means is readily repositionable relative to said control head housing means so that an operator can reposition said entry block means to a suitable position relative to said housing means for using said working channel.

2. An instrument as in claim 1 wherein said means for repositionally mounting said entry block means has a limiting stop means to limit the amount of reposition.

3. An instrument as in claim 2 wherein said means for repositionally mounting said entry block means is limited to about a 90 degree repositioning arc relative to said control head.

4. An instrument as in claim 1 wherein said entry block means is sealingly engaged on said control head housing means.

5. An instrument as in claim 1 wherein said entry block means includes an entry tube and entry tube retainer.

6. An instrument as in claim 1 wherein said entry block means includes a stopcock adaptor.

7. An instrument as in claim 1 wherein said entry block means includes a stopcock.

8. An instrument of a generally tubular flexible shape for accessing a target area, said instrument having a proximal end thereof, a distal end thereof, and a working channel therebetween , said proximal end having a control head, said control head further comprising:

control head housing means, repositionable entry block means having a passageway to permit access of said working channel from said entry block means through said control head, and mounting means movably interconnecting said control head housing and said entry block means to enable said entry block means to be repositioned relative to said control head housing whereby an operator is able to reposition said entry block means to a suitable position for using said working channel.

9. An instrument as in claim 8 wherein said mounting means has a means for limiting the amount of entry block means reposition.

10. An instrument as in claim 8 wherein said entry block means is sealingly engaged on said control head housing.

11. An instrument as in claim 8 wherein said entry block means includes an entry tube and entry tube retainer.

12. An instrument of a generally tubular shape for accessing a target area, said instrument having a proximal end thereof, a distal end thereof, and a working channel therebetween, said proximal end having a control head, said control head further comprising:
  control head housing means,
  repositionable entry block means having a passageway to permit access of said working channel from said entry block means through said control head, and
  repositionable light carrier entry means for enabling a light carrier means to enter into said control head.

* * * * *